United States Patent [19]

Landvogt

[11] Patent Number: 5,549,591

[45] Date of Patent: Aug. 27, 1996

[54] ADHESIVE/MECHANICAL FASTENER SYSTEMS FOR DISPOSABLE ARTICLES

[75] Inventor: Brigitte Landvogt, Euskirchen-Kirchheim, Germany

[73] Assignee: The Procter & Gamble Company, Cincinnati, Ohio

[21] Appl. No.: 313,138

[22] PCT Filed: Mar. 19, 1993

[86] PCT No.: PCT/US93/02531

§ 371 Date: Dec. 15, 1994

§ 102(e) Date: Dec. 15, 1994

[87] PCT Pub. No.: WO93/19713

PCT Pub. Date: Oct. 14, 1993

[30] Foreign Application Priority Data

Apr. 2, 1992 [EP] European Pat. Off. ............ 92200943.6

[51] Int. Cl.[6] .................................................. A61F 13/15
[52] U.S. Cl. ............................................ 604/389; 604/391
[58] Field of Search .................................. 604/389, 390, 604/391

[56] References Cited

U.S. PATENT DOCUMENTS

| 5,019,065 | 5/1991 | Scripps | 604/391 |
| 5,288,546 | 2/1994 | Roessler | 604/391 |
| 5,383,872 | 1/1995 | Roessler | 604/391 |
| 5,403,302 | 4/1995 | Roessler | 604/391 |

*Primary Examiner*—Michael J. Milano
*Attorney, Agent, or Firm*—David M. Weirich; Kevin C. Johnson; Steven W. Miller

[57] ABSTRACT

The present invention relates to tape tab fastener systems for disposable absorbent articles (20). More particularly it relates to tape tab fastener systems combining mechanical and adhesive tape tab fastener (60) in a design comprising a short release tape (65) and a delamination introducing zone (67) between the adhesive (63) and the mechanical (62) fastening member on the tape tab fastener. The invention provides improved handling characteristics, improved construction stability compatibility with compression packaging.

15 Claims, 2 Drawing Sheets

ADHESIVE/MECHANICAL FASTENER SYSTEMS FOR DISPOSABLE ARTICLES

FIELD OF THE INVENTION

The present invention relates to tape tab fastener systems for disposable absorbent articles. More particularly to tape tab fastener systems combining mechanical and adhesive tape tab fastener means in a design with improved handling characteristics, improved construction stability, compatibility with compression packaging. In particular it comprises a short release tape which is protected against full or partial detachment from its foundation.

BACKGROUND OF THE INVENTION

The use of tape tab fastener systems for securing the corners of disposable absorbent articles such as diapers or incontinents briefs is well known in the art. Examples of adhesive tape tab fastener systems are disclosed in U.S. Pat. No. RE 26,151, U.S. Pat. No. 3,848,594 and many other publications. While adhesive tape tab fastener systems did provide secure means for fixing a disposable absorbent article around a user's waist during use they were not totally satisfactory.

Adhesive tape tab fastener systems were often only usable upon initial fixation of the disposable absorbent article while refastening was not possible. They also displayed unsatisfactory resistance against contamination.

Hence the prior art discloses many alternative fastener systems trying to solve these problems. For example mechanical fastener systems of the hook/loop type (random entanglement) have been contemplated and disclosed in many publications. In general mechanical fastener systems have the advantage of reduced or no sensitivity versus contamination for example by oils or powders. Mechanical hook/loop fastener systems also have the advantage of being reclosable after opening for example to check the soiling of absorbent articles or to correct the fitting of absorbent articles on the wearer. However, mechanical fasteners require a two part fastening system e.g. tape tabs with hooks and a landing surface with loops.

Mechanical tape tab fasteners of the hook/loop type have been disclosed for use in diapers for example in U.S. Pat. No. 3,110,312 and for disposable diapers in U.S. Pat. No. 4,259,957 or European Patent Application EP-A-235014.

After establishing the principal advantages of mechanical fasteners over adhesive tape tab fasteners, it was found that mechanical fasteners lack the ease of disposability which the adhesive tape tab fasteners provided for disposable absorbent articles. Before disposing a used disposable absorbent article the article is often rolled up upon itself. This pack is then closed by applying the adhesive tape tab onto the outside surface of the rolled up disposable absorbent article.

The advantage of disposability is supplied by adhesive tape tabs which can be attached anywhere to the disposable absorbent article. Mechanical hook/loop fasteners by design require their respective counter surface to achieve an attachment. However, when rolling a disposable diaper onto itself one of the two mechanical fastening members, usually the landing member, is inside the roll and hence unaccessable.

Attempts to resolve this disposability problem have resulted in tape tab fastener systems combining mechanical and adhesive parts. Disclosure of such adhesive-mechanical tape tab fastener systems can be found for example in European Patent Applications EP-A-321232 or EP-A-324578. Adhesive-mechanical fastener systems have the combined advantages of low sensitivity versus contamination and exceptionally good reclosure performance as well as easy disposal of the absorbent article after use. However they still exhibit certain problems which only now have been defined and which are solved by the present invention.

Most adhesive-mechanical tape tab fasteners are in principle made like regular adhesive tape tab fasteners but include a mechanical fastener member on the adhesive tape surface. The adhesive of the tape is used to join the mechanical fastener member to the adhesive-mechanical tape tab fastener. In the process of making a disposable absorbent article the adhesive mechanical tape tab fastener is usually folded inwards into a so called packaging or transport position. In this position the adhesive member of the tape tab fastener requires a countersurface which would easily release the adhesive tape when the article is used. Usually, the countersurface is provided by placing a single sided adhesive tape, called release tape, in the respective release area. The adhesive side of the release tape provides its foundation and the non-adhesive reverse side provides the release function for the adhesive part of the tape tab fastener.

In European Patent Application 89201611.4 and 90202696.2 packages containing flexible articles such as disposable diapers have been disclosed in which the diapers are under up to 60% compression. These compression packages have since then become widely used, particularly since they reduce packaged volume and packaging material consumption while containing the same number of diapers as the historically used uncompressed packages. During packing very high pressures have to be exerted on the disposable absorbent articles to achieve the volume reduction necessary for making compression packages.

When having been packed into compression packages disposable absorbent articles with adhesive-mechanical tape tab fastener systems of the designs disclosed in the prior art often exhibit the problem of reduced mechanical fastening performance. It is believed that for diapers with mechanical fastening members comprising protruding elements like hooks or loops, this problem is due to the bending, weakening or destruction of at least some of the hooks or loops during compression.

It has now been found that the complex fastener system with release tape causes problems for the mechanical member integrity in conjunction with compressed packaging when the release tape and the mechanical fastening member have co-extensive areas in a transport position. If on the other hand this is prevented and the release tape is co-extensive with or smaller than the adhesive fastening member, problems of full or partial release tape detachment from the material to which the release tape is adhered have been exhibited. If the adhesion of the release tape to the underlying material is strong enough the underlying material may even be damaged thereby rendering the absorbent article useless. Both of these problems, which are calling for contradicting solutions, are solved and addressed by the current invention.

An objective of the present invention is to provide adhesive-mechanical tape tab fasteners for disposable absorbent articles which maintain the mechanical fastener member's integrity during manufacturing and packaging, in particular for disposable absorbent articles which are compression packed.

Another objective of the present invention is to provide an optimised fastening system having a reduced release tape length and a delamination introducing area to protect the release tape from becoming detached.

Another objective of the present invention is to provide an adhesive-mechanical tape tab fastener system having the afore-mentioned advantage at no increase or even at reduced material consumption to satisfy regulatory and user demands for ecological and economical fastening systems for disposable absorbent articles.

These and other objectives of the present invention will be more readily apparent from the following description and the accompanying drawings.

SUMMARY OF THE INVENTION

According to the present invention, the disposable absorbent article such as a baby diaper or an adult incontinent brief is provided with a mechanical-adhesive tape tab fastener system. The absorbent article has an outside surface and an inside surface. The fastener system comprises a tape tab which is joint to the disposable absorbent article in a first end region with the fastener's manufacturing region, preferably by an adhesive. The free or user's end of the tape tab comprises two fastening members: a mechanical fastening member and an adhesive fastening member.

The mechanical fastening member represents the primary closure system of the absorbent article during wearing. When the absorbent article is worn, the mechanical part of the fastening system operates by overlapping the mechanical fastening member on the tape tab onto a landing member which is designed to mechanically entangle with the mechanical fastening member of the tape tab. Particular preferred are hook type mechanical fastening members on the tape tab to be randomly entangled with loop type landing members. The landing member is disposed on the outside surface in the second end region of the absorbent article such that the disposable absorbent article can be wrapped around the wearer's hips and closed around the side of the wearer by use of the mechanical fastening member of the tape tab fastener and the landing member.

The adhesive fastening member provides the desired disposability function when the disposable absorbent article is rolled up into a neat package after use which is closed by placing the adhesive member anywhere on the outside surface of the absorbent article.

During transport of the disposable absorbent article the mechanical-adhesive tape tab fastener are fully folded onto the inside surfaces of the disposable absorbent article so as to not extend outside the body portion of the absorbent article. In this transparent configuration the adhesive and mechanical fastening members rest with their active sides well protected on the body size surface of the absorbent article. In order to protect the adhesive fastening member a release tape is disposed on the inside surfaces of the absorbent article, such that the adhesive surface of the adhesive fastening member is fully covered by the release side of the release tape. The position and the dimension of the release tape have to be selected to extend at most such that the release tape has no overlap with the engagement elements of the mechanical fastening member in accordance with a copending European patent application entitled "Adhesive-Mechanical Fastener Systems for disposable absorbent articles", by the inventors being B. Landvogt and D. Bullesfeld, filed on the same day as the present application.

When using the disposable absorbent article the tape tab is pulled away from the release tape thereby delaminating the adhesive fastening member from the release tape. To ensure that this delamination does not cause full or partial detachment of the release tape from its foundation a delamination introducing area has to be provided in which the delamination can start without causing the above objectionable detachment. According to the present invention this delamination introducing area is provided as a non adhesive surface on the tape tab. This surface extends across the full longitudinal dimension of the tape tab and is placed in lateral direction between the mechanical fastening member and the adhesive fastening member. According to the invention, the non-adhesive surface is disposed such that in the transport configuration it extends in lateral direction over the lateral inward edge of the release tape. Preferably it extends from 3 to 10 mm, most preferably from 5 to 7 mm in lateral direction from the lateral inward edge over the release tape.

DETAILED DESCRIPTION OF THE INVENTION

Figure 1:
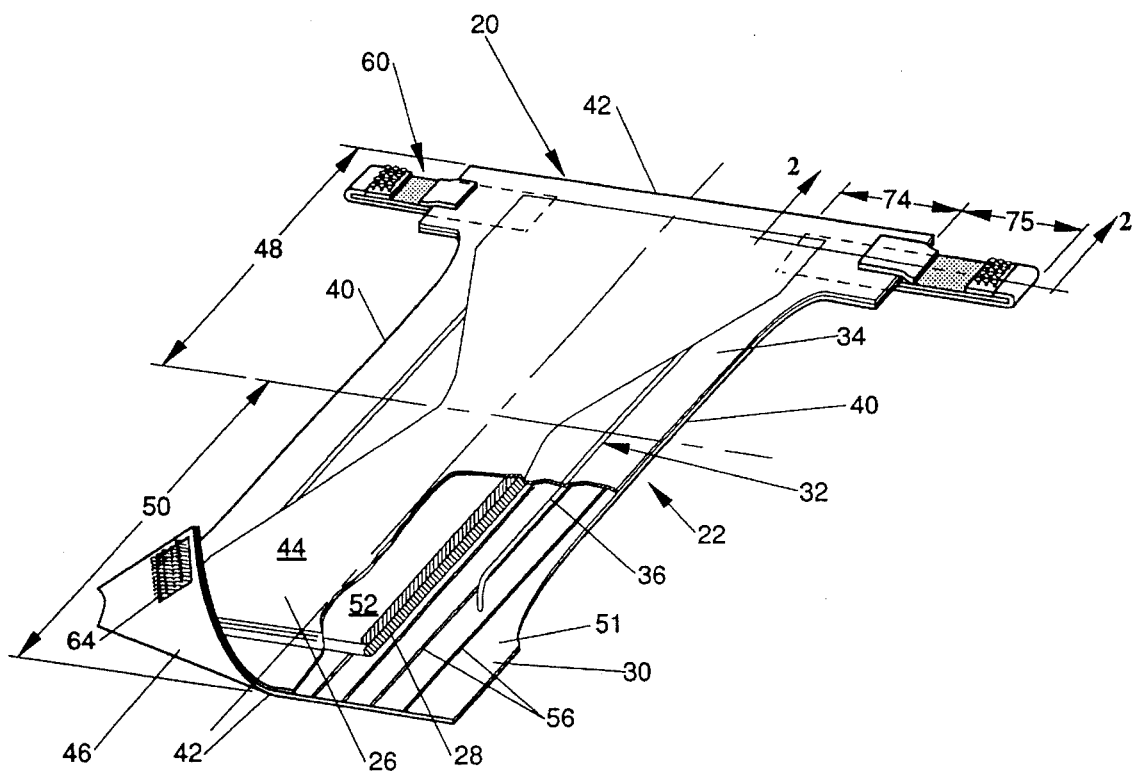
FIG. 1 is a partially cut-away perspective view of a preferred diaper embodiment incorporating the present invention.

Adhesive mechanical fastener systems of the present invention are useful and beneficial when applied to disposable absorbent articles. As used herein the term "disposable absorbent articles" refers to articles which absorb and contain body exudates and more specifically refers to articles which are placed against or in the proximity of the wearer's body to absorb and contain the various exudates discharged from the body of the wearer and which are not intended to be laundered or otherwise restored or reused as an absorbent article (i.e. they are intended to be discarded after a single use and, preferably to be recycled, composted or otherwise disposed of in an environmentally compatible manner). A preferred embodiment of the disposable absorbent article of the present invention is an adult incontinence brief or a baby diaper, as shown in FIG. 1 as diaper (20). As used hereinafter the term "diaper" refers to an absorbent article generally worn by infants or incontinent persons that is drawn up between the legs and fastened about the waist of the wearer. Examples of the kind of diapers to which the present invention is readily adapted are shown in U.S. Pat. No. RE 26,151; U.S. Pat. Nos. 3,860,003; 4,253,461; and 7,704,115. It will be apparent from the following description that the adhesive-mechanical fastener system illustrated and described herein, could be applied to the body portion on such diapers. On the other hand, it will be understood that the invention is not limited to any specific diaper structure or configuration, provided it has a fastening system and is compatible with the requirements of the disposable absorbent articles disclosed herein.

Referring to the drawings, it will be noted that FIG. 1 is a partially cut-away perspective view of the diaper (20) according to the present invention prior to its being placed on a wearer. As can be seen in FIG. 1, a preferred diaper (20) comprises an adhesive-mechanical tape tab fastener, designated generally as (60). A preferred body portion (22) comprises a liquid pervious topsheet (26), an absorbent core (28), a liquid impervious backsheet (30), and elastically contractible leg cuffs (32) comprising a side flap (34) and one or more elastic members (36). For simplicity purposes, only 1 elastic member is shown in the side flap (34). While the topsheet (26), the absorbent core (28), the backsheet (30), the side flaps (34), and the elastic members (36) may be assembled in a variety of well-known configurations. A preferred diaper configuration is shown and described generally in the above referenced U.S. Pat. No. 3,860,003 or 4,253,461.

FIG. 1 shows a preferred embodiment of the body portion (22) in which the topsheet (26), the backsheet (30) are coextensive and have length and widths dimensions generally larger than those of the absorbent core (28). The topsheet (26) is superposed to the backsheet (30) thereby forming the periphery of the body portion (22).

The periphery defines the outer primeter or in other words the outer extent of the body portion (22). The periphery comprises the longitudinal side edges (40) and the first and second lateral end edges (42). In longitudinal direction the diaper (20) has a first end region (48) and a second end region (50).

The body portion (22) has an inside surface (44) and an outside surface (46). In general, the outside surface (46) of the diaper (20) extends from a first lateral end edge (42) to a second lateral end edge (42) of the diaper (20) and from one longitudinal side edge (40) to the other longitudinal side edge (40) of the diaper. The outside surface (46) usually is the surface farthest from the wearer during use of the diaper (20). The backsheet (30) preferably forms most of the outside surface (46) of the body portion (22). The inside surface (44) is that surface of the diaper (20) opposite the outside surface (46) and in the embodiment shown in FIG. 1 is preferably formed by the topsheet (26). Preferably, the inside surface (44) of the diaper (20) is coextensive with the outside surface (46) and in general the inside surface (44) is for the greater part in contact with the wearer when the diaper (20) is used.

The diaper (20) has first and second end regions (48 and 50, respectively), extending from the first and second end edges (42) of the diaper periphery towards the lateral center line of the diaper (20). Both the first end region (48) and the second end region (50) extend a distance of about ½ of the length of the diaper (20) such that the end regions each comprise half of the diaper (20).

The absorbent core (28) of the body portion 22 may be any absorbent means which is generally compressible, conformable, non-irritating to the wearer's skin, and capable of absorbing and retaining liquids such as urine and other certain body exudates. The absorbent core (28) may be manufactured in a wide variety of sizes and shapes (e.g., rectangular, hourglass, asymmetric, T-shaped, etc.) and from a wide variety of liquid absorbent materials commonly used in diapers and other disposable absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials or any equivalent materials or combination of materials. The configuration and construction of the absorbent core may also be varied e.g., the absorbent core may have varying caliper zones, a hydrophillic gradient, a superabsorbent gradient (as in concentration or particle size for granular superabsorbents), or lower average density and lower average basis weight acquisition zones; or may comprise one or more layers or structures. The total absorbent capacity of the absorbent core (28) should, however, be compatible with the design exudate loading and the intended use of the diaper (20). Further, the size and absorbent capacity of the absorbent core (28) may be varied to accomodate wearers ranging from infants to adults.

A preferred embodiment of the diaper (20) has an hourglass-shaped absorbent core (28). An exemplary absorbent structure for use as the absorbent core is described in U.S. Pat. Nos. 4,610,678, 4,673,402, 4,888,231. The absorbent core (28) is preferably the commercially successful absorbent member described in U.S. Pat. No. 4,834,735, entitled "High Density Absorbent Members Having Lower Density and Lower Basis Weight Acquisition zones". Other preferred absorbent cores are described in U.S. Pat. Nos. 4,685,915 and 4,781,710 as comprising fibrous structures having areas of different absorbent capacity, density, or liquid acquisition speed. An alternative thin absorbent core useful in the present invention may be found in U.S. Pat. No. 4,600,458. Another preferred absorbent core design provides for a crosslinked cellulose patch essentially without superabsorbent on top of an airfelt with superabsorbent mixture comprising more than 30% superabsorbent.

The absorbent core (28) is superposed on the backsheet (30) and is preferably joined thereto by a core attachment means (not shown) such as those well known in the art, for example, pressure-sensitive adhesives, hot melt adhesives or other adhesives; ultrasonic bonds; heat/pressure bonds, dynamic mechanical bonds; or any other suitable attachment means or combinations of these attachment means as are known in the art. For example, the absorbent core (28) may be secured to the backsheet (30) by a uniform continuous layer of adhesive, a patterned layer of adhesive, or a network of adhesive filaments such as any array of random lines, separate lines, spirals, or spots of adhesive. Adhesives which have been found to be satisfactory are preferably hot melt adhesives such as manufactured by Century Adhesives, Inc., of Columbus, Ohio and marketed under the tradename Century 5227; and by H. B. Fuller Company of St. Paul, Minn. and marketed as HL-1258. The core attachment means preferably comprise an open pattern network of filaments of adhesive as is shown in U.S. Pat. No. 4,573,986 entitled "Disposable Waste-Containment Garment". An exemplary attachment means of an open pattern network of filaments comprises several lines of adhesive filaments swirled into a spiral pattern such as is illustrated by the apparatus and methods shown in U.S. Pat. Nos. 3,911,173, 4,785,996 or 4,842,666.

The backsheet (30) is impervious to liquids (e.g. urine) and is preferably manufactured from a thin plastic film, preferably a thermoplastic film, although other flexible liquid impervious materials may also be used. As used herein, the term "flexible" refers to materials which are compliant and which will readily conform to the general shape and contours of the human body. The backsheet (30) prevents the exudates absorbed and contained in the absorbent core (28) from soiling articles which contact the diaper (20) such as bedsheets and undergarments. The backsheet may thus comprise polymeric films such as thermoplastic films of polyethylene or polypropylene, or composite materials such as a film-coated nonwoven material. For economic, aesthetic, and ecological reasons, the backsheet (30) preferably has an average nominal caliper, i.e. calculated caliper, of less than about 0.051 mm, more preferably a calculated caliper of from 0.020 mm to 0.036 mm. Preferably, the backsheet (30) is a flexible polyethylene film. As used herein the term "polyethylene" film refers to films which are essentially made of polyethylene, however, it is understood that polyethylene film will contain a variety of additives to provide characteristics like opacity, strength requirements, color, or any other desired characteristic that can be achieved through adding minor amounts of other substances than polyethylene into the films. The total amount of additives should be less than 45%, preferably less than 15%, by weight of film materials. Particularly for opacity of the film, titanium dioxide is commonly used in a range of 2–6%, preferably 3.5–4.8%, by weight of the film. Exemplary films for use as the backsheet of the present invention are manufactured by Tredegar Industries, Inc. of Terre Haute, Ind., USA or BP-Chemical PlasTec Rotbuchenstrasse 1 D- 8000 MÜNCHEN, Germany.

The backsheet (30) is preferably textured to provide a more clothlike appearance. Further, the backsheet (30) may also permit vapors to escape from the absorbent core (28) while still preventing exudates from passing through the backsheet (30) by ,for example, being supplied with microapertures as described, for example, in U.S. Pat. No. 4,681,793. The backsheet may also be biodegradable such as the film disclosed in U.S. patent application Ser. No. 07/721, 066 entitled "Disposable Absorbent Articles with Biodegradable Backsheets".

The size of the backsheet (30) is dictated by the size of the absorbent core (28) and the exact diaper design selected. In a preferred embodiment, the backsheet (30) has a modified hourglass shape extending beyond the absorbent core a minimum distance of at least 1.3 cm to 2.5 cm for baby diapers and 1.3 cm to 6 cm for adult incontinent briefs around the entire diaper periphery.

The topsheet (26) of the body portion (22) of the present invention is compliant, soft feeling, and non-irritating to the wearer's skin. Further, the topsheet (26) is liquid pervious permitting liquids (e.g. urine) to readily penetrate through its thickness. A suitable topsheet (26) may be manufactured from a wide range of materials, such as porous foams, reticulated foams, apertured films; or woven or nonwoven webs of natural fibers (e.g. wood or cotton fibers), synthetic fibers (e.g. polyester or polypropylene fibers) or from a combination of natural and synthetic fibers. Preferably, it is made of a material that isolates the wearer's skin from liquids retained in the absorbent core (28).

There are a number of manufacturing techniques which may be used to manufacture the topsheet (26). For example, the topsheet (26) may be a non-woven web of fibers. When the topsheet comprises a nonwoven web, the web may be spunbonded, carded, wet-laid, meltblown, hydroentangled, hydroformed, combinations of the above, or the like. An exemplary topsheet (26) is carded and thermally bonded by means well known to those skilled in the fabric art and comprises staple length polypropylene fibers having a denier of about 2.2 and has a basis weight from about 15 to about 30 grams per square meter. As used herein, the term "staple length fibers" refer to those fibers having a length of at least about 16 mm. A suitable topsheet is manufactured for example by Veratec, Inc., a Division of International paper Company, of Walpole, Mass. under the designation P-8. A topsheet particularly preferred for incontinent briefs of the present invention, comprises a formed thermoplastic film such as that described in U.S. Pat. No. 3,929,135 entitled "Absorptive Structure Having tapered Capillaries".

The topsheet (26) and the backsheet (30) are joined together in any suitable manner as is well known in the diaper manufacturing art. As used herein, the term "joined" encompasses configurations whereby the topsheet (26) is directly joined to the backsheet (30) by affixing the topsheet (26) directly to the backsheet (30), and configurations whereby the topsheet (26) is indirectly joined to the backsheet (30) by affixing the topsheet (26) to intermediate members (e.g. absorbent core (28)) which in turn are affixed to the backsheet (30). In a preferred embodiment, the topsheet (26) and the backsheet (30) are joined directly to each other in the diaper periphery by a flap attachment means such as an adhesive or any other attachment means as is known in the art. In general, the core attachment means that affixes the absorbent core (28) to the backsheet (30) is the same means as the flap attachment means (56) that affixes the topsheet (26) to the backsheet. Thus, for example, a uniform continuous layer of adhesive, a patterned layer of adhesive, an array of separate lines, spirals, or spots of adhesive such as a network of adhesive filaments such as shown in U.S. Pat. No. 4,573,986, may be used.

The diaper (20) preferably further comprises elasticized leg cuffs (32) for providing improved containment of liquids and other body exudates. Each elasticized leg cuff (32) may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions for a disposable diaper" describes a disposable which provides a contractible leg opening having a side flap and elastic members to provide an elasticized leg cuff (gasketing cuff). U.S. Pat. No. 4,909,803 entitled "Disposable absorbent article having elasticized flaps" describes a disposable diaper having "stand-up" elasticized flaps (barrier cuffs) to improve the containment of the leg regions. U.S. Pat. No. 4,695,278 entitled "Absorbent article having dual cuffs" describes a disposable diaper having dual cuffs including a gasketing cuff and a barrier cuff. U.S. Pat. No. 4,704,115 entitled "Disposable waist Containment garment" discloses a disposable diaper or incontinent garment having side-edge-leakage-guard gutters configured to contain free liquids within the garment. While each elasticized leg cuff (32) may be configured so as to be similar to any of the leg bands, side flaps, barrier cuffs, or elastic cuffs described by above disclosures, it is common for the present invention that each elasticized leg cuff (32) comprises a side flap (34) and one or more elastic members (36) such as shown in FIG. 1.

The diaper may also further comprise an elastic waist feature (not shown in FIG. 1) that provides improved fit and containment or any other features typically provided on diapers or incontinent garments as are known in the art. An exemplary elasticized waist feature is described in U.S. Pat. No. 4,515,595.

The diaper (20) is provided with an adhesive-mechanical fastening system for forming a side closure on each side of the diaper (20). Thus, the diaper (20) is fitted to the wearer and the first end region (48) and the second end region (50) are maintained in an overlapping configuration when the diaper (20) is worn such that lateral tensions are maintained around the circumference of the diaper to maintain the diaper on the wearer.

Figure 2:
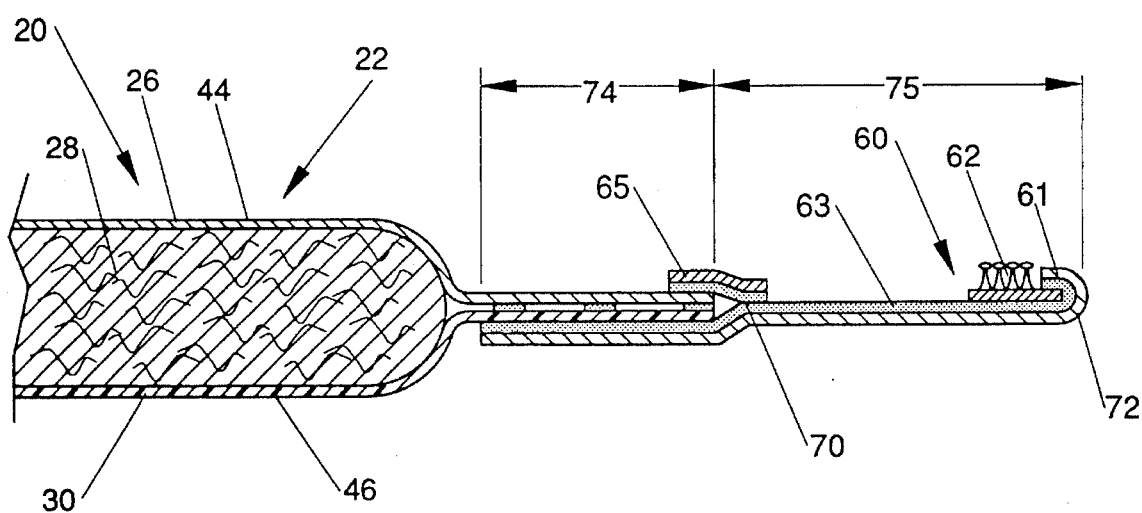
FIG. 2 is a cross-sectional view of the corner of the diaper taken along line 2—2 of FIG. 1.

According to the present invention as shown in FIG. 1, the fastening system comprises two elements, an adhesive-mechanical tape tab fastener (60) and a landing member (64) which are joined to each other during use. The tape tab has a manufacturer's region (74) and a user's region (75). The tape tab fastener (60) is disposed in the first lateral end region (48) such that the manufacturer's region (74) is joined to the absorbent article (20) and the user's region (75) extends beyond the longitudinal side edge (40) of the absorbent article (20). The user's region (75) has a proximal region which comprises an adhesive fastening member (63) and it has a distal region which comprises a mechanical fastening member (62) and preferably a grip-tab (61). As shown in FIG. 2, the manufacturer's region (74) of the tape tab fastener (60) is preferably joined to the outside surface

(46) of the absorbent article (20). However, it can also be sandwiched between the topsheet (26) and the backsheet (30) of the absorbent article (20).

As shown in FIG. 2 of the present invention, the tape tab fastener (60) further comprises a release tape (65). The release tape is disposed such that the tape tab fastener (60) in its transport configuration, that is when the tape tab fastener (60) is folded along the separating line of the manufacturer's region (74) and the user's region (75) onto itself towards the inside surface (44) of the absorbent article (20), provides a release surface to the adhesive fastening member (63) in order to protect the adhesive fastening member (63) from contamination and in addition to maintain the folded tape tab fastener (60) in its packaged position. The release tape (65) is designed such that the fastening surface, that is the surface of the engaging elements of the mechanical fastening member (62) is not in contact with the release surface of the release tape (65) when the tape tab fastener (60) is in its transport configuration.

For defect free and convenient handling upon use of an absorbent article according to the present invention it is necessary that in the transport position the adhesive contact area between the adhesive fastening member (63) and the release tape (65) does not extend in lateral direction all the way to the laterally inward end (66) of the release tape (65). The preferred distance between the laterally inward ends of the adhesive contact area and the release tape that is a non-adhesive lateral length of a delamination introducing area (67) is from 3 mm to 10 mm, most preferred 5 mm to 7 mm. A distance of 6 mm has been found to provide satisfactory performance.

In a preferred embodiment the release tape (65) extends slightly beyond the longitudinal side edge (40) into the user's region (75) of the tape tab fastener (60) and is joined, preferably by adhesive to adhesive attachment in a Y-bond (70) to the adhesive fastening member (63) of the tape tap fastener (60).

The grip-tab (61) can be provided by an additional piece of material which is disposed from the laterally outward edge (72) of the user's region (75) and preferably extends over at least part of the mechanical fastening member (62). It is however preferred that the grip-tab (61) is formed by folding the laterally outward edge (72) of the user's region (75) back onto itself and over part of the mechanical fastening member (62). The overlap of the grip-tab (61) with the mechanical fastening member (62) provides the mechanical fastening member (62) with an additional attachment to the tape tab fastener (60).

In a preferred embodiment as shown in FIG. 2 of the tape tap fastener (60) of the present invention, the tape tab fastener has a continuous adhesive tape material extending from the manufacturer's region (74) to the user's region (75) thereby providing the adhesive fastening member (63) without additional materials and comprises a grip-tap (61) which is folded over onto itself and onto the mechanical fastening member (62). It also comprises a Y-bond. Y-bond constructions are shown and explained in detail in U.S. Pat. No. 3,848,594 entitled "Tape fastening system for disposable diapers".

According to the invention the adhesive free surface providing the delamination introducing area (67) in a transport position can be formed in several different ways. For example, tapes having a selectively coated adhesive which leaves the delamination introducing area (67) free of adhesive can be used. Alternatively, if the above mentioned continuous adhesive tape material is used the adhesive surface in the delamination introducing area (67) can be rendered non-adhesive by designed contamination for example with grease, talcum or similar. Instead another strip of material independent of the remaining tape construction can be introduced to cover the adhesive in this delamination introducing area (67). Most preferred however is to simply extend the mechanical fastening member (62) such as to cover the delamination introducing area when using a continuous adhesive tape material. As will become clear when describing the mechanical fastening member this can be achieved without sacrificing the advantage of having a release tape which does not extend into the fastening relevant area of the mechanical fastening member.

The fastening-landing member (64) for corporation with the mechanical fastening members is disposed in the second lateral end region (50) and joined to the outside surface (46) of the diaper (20). The landing member (64) can be a unitary material to which all tape tab fasteners of the diaper (20) are attached during use. However, as indicated in FIG. 1, the landing member (64) can also be provided in smaller, more economical and ecological sizes depending on the use for which the absorbent article is designed.

The tape tab fastener (60) comprises a tape backing material which can be any of the tape backing materials well known in the art. For example, polyester films, polypropylene films, paper backings, or other materials which provide the required strength to be useful as part of a tape tab fastener (60) during use of a diaper (20) are suitable for use as the tape backing material. Particularly, tape backing materials of polypropylene film having a caliper of about 0.15 mm have been found to perform satisfactorily. The same materials used for the tape tab backing material can be used for the release tape (65). In order to perform its release function, the side of the release tape that is not attached to the inside surface (44) can be coated with a release agent, preferably with a silicone release coating, which is well known in the art.

The tape tab fastener has an adhesive fastening member (63) having a layer of adhesive coated onto the tape backing material. (As used herein, the term "coated" is not to be limited to any specific technique or method for applying the adhesive onto the tape backing material). The adhesive fasting member may use any suitable adhesive that provides the desired attachment strength required for its disposability function. The composition of the adhesive for the adhesive fastening member (63), is not as important as the properties of the overall tape tab fastener (60). The adhesive can, for example, be a hot melt adhesive which is coated onto the tape backing by any of the well known hot melt coating processes (e.g. by a slot coating process). Alternatively, the adhesive can be supplied in a solvent coating process. Preferably, the adhesive is an elastomeric pressure-sensitive adhesive. It is particularly preferred that such an adhesive material comprises a tackified rubber elastomer. In accordance with the present invention, it has been found that tapes such as are manufactured by the Minnesota Mining and Manufacturing Company, St. Paul, Minn., under the designation XPF 14.43.0, Y-9376 or Y-9030 for the tape backing material and XPF 1.42.34 for the adhesive, have been found to provide satisfactory performance in the tape tab fasteners of the present invention.

The joining of the manufacturer's region (74) to the body portion (22) can be provided by mechanical or preferably by adhesive means. In a preferred embodiment, the tape backing of the tape tab fastener (60) is coated on its whole surface with a layer of adhesive. This adhesive, thus, not only provides the adhesive fastening member (63) but also the attachment to permanently adhere the manufacturer's region (74) to the outside surface (46), preferably to the backsheet (30). If the adhesive further is coated also laterally outside the adhesive fastening member (63), it provides the means for joining the mechanical fastening member (62) to the tape backing and the possibility to fold over the outside edge of the tape tab fastener (60) onto itself thus forming the grip-tap (61).

Even so less preferred versus adhesive means to secure the manufacturer's region (74) to the body portion (22) mechanical means are well known in the art and can be used. For example ultrasonic bonding or welding by use of heat and/or pressure energy are useful in this context.

The mechanical fastening member (62) of the adhesive-mechanical tape tab fastener (60) preferably comprises a hook fastening material as its fastening relevant part. As used herein the term "hook fastening material" is used to designate a material having engaging elements. The hook fastening material (62) may also be referred to as male fastener. It should be understood that the use of the term "hook" should be non-limiting in the sense that the engaging elements may comprise any shapes as are known in the art as long as they are adapted to engage a complementary second fastening element which is comprised in the landing member (64). The hook fastening material preferably comprises a base having a first surface and a second surface and a plurality of engaging elements extending from the first surface of the base. The area in which these engaging elements extend from the base have been termed fastening surface of the mechanical fastening member. It is particularly preferred, as shown in FIG. 2, that the mechanical fastening member (62) has the engaging elements extend only from part of the base and that a laterally extending part of the base provides the delamination introducing area (67) according to the invention.

The preferred hook fastening material (62) of the present invention is intended to engage a fibrous element of a loop fastening material so as to provide a secure fastening device. Thus, hook fastening material (62) may be manufactured from a wide range of materials. Suitable materials include nylon, polyester, polypropylene or any combination of these materials. A suitable hook fastening material (62) comprises a number of shaped engaging elements projecting from an extruded film backing or a woven backing such as the commercially available material designated Scotchmate Brand (TM) number FJ 3402 available from Minnesota Mining and Manufacturing Company, St. Paul, Minn., USA. Alternatively the engaging elements may have any shape such as hooks, "Ts", mushrooms or any other shape as are well known in the art. A particular preferred hook fastening material (62) is described in European Application EP-A-276970.

The landing member (64) preferably comprises a fastening element which is engagable with the mechanical fastening member (62). The fastening elements of the landing member (64) may be manufactured from a wide range of materials and configurations capable of securily engaging the mechanical fastening member (62). For example it may comprise identical complementary elements with the mechanical fastening member (62) or distinct complementary elements with the mechanical fastening member (62). As used herein, the term identical complementary elements is used to define mechanical fastening systems wherein the engaging elements of the two fastening members of the mechanical fastener comprise the same configuration or structure that are interlocking. Examples of such systems are described in U.S. Pat. No. 4,322,875 or 4,701,179. The term "distinct complementary elements" is used herein to designate a system wherein the mechanical fastening member (62) is different from the landing member (64) but is engagable such as buttons and holes a hook fastening material and a loop fastening material or a male member and a female member. Preferably, the landing member (64) comprises a hook fastening material or a loop fastening material depending upon whether the mechanical fastening member (62) is a loop fastening material or a hook fastening material. The landing member (64) preferably comprises a plurality of fibrous elements as loop fastening material.

The loop fastening material of the landing member (64) provides a plurality fibre elements that engage the engaging elements of the hook fastening materials (62). The loop fastening material may be manufactured from a wide range of materials to provide fibre elements, preferably loops. Such suitable materials include nylon, polyester, polypropylene, or any combination of these materials. A suitable loop fastening material for a landing member (64) comprises a number of fibre loops projecting from a woven backing such as the commercially available material designated Scotchmate brand (TM) nylon, woven loop number SJ 3401 available from Minnesota Mining and Manufacturing Company, St. Paul, Minn., USA. A preferred loop fastening material comprises a tricot knit fabric having a plurality of nylon filament loops projecting from a backing of nylon such as the commercially available material designated "Guilford No 16110" (TM) available from Guilford Mills of Greenborough, N.C., USA. Alternatively, the loop fastening material of the landing member (64) may be a non-woven fabric or any other type of fibre material or loop material which are well known in the art. An inexpensive loop fastening material and a method of making such a loop fastening material is described in European Patent Application EP-A-289198.

The landing member (64) or as shown in FIG. 1 the landing members (64) as well as the mechanical fastening member (62) can be joined in their respective places on the diaper (20) by any of the afore-mentioned mechanical or adhesive means.

In use the diaper (20) is applied to the wearer by positioning the first end region (48) under the wearer's back and drawing the remainder of the diaper (20) between the legs of the wearer so that the second end region (50) is positioned across the front of the wearer. Mechanical fastening member (62) of the fastening tape tabs (60) are then secured to the landing members (64) positioned on the outside surface (46) of the second end region (50) so that the mechanical fastening member (62) will engage the fastening elements with the fastening elements of the landing member (64) and the adhesive fastening member (63) is not exposed to contamination by lightly adhering to the outside surface (46) of the diaper (20) or to the landing member (64) whichever is disposed below it. After the diaper (20) has been soiled, the diaper (20) is removed from the wearer. The side panels (51) in the second end region (50) may then be folded in and the body portion (22) beginning with the second end region (50) folded or rolled into a structure with the adhesive-mechanical tape tab fastener (60) still extending outwardly from the rolled up diaper (20). The adhesive fastening member (63) is then secured to either the other tape tab fastener (60) or to the backsheet (30) so as to secure the diaper (20) in its rolled up configuration such that it may be easily and conveniently disposed in a waste reciptical.

What is claimed is:

1. A disposable absorbent article having a transport configuration when packaged and during transport, said absorbent article comprising:

a body portion having an inside surface and an outside surface, side edges extending in a longitudinal direction, a first end region and a second end region;

an adhesive-mechanical fastening tape tab positioned in said first end region of said body portion and comprising a manufacturer's region and a user's region; said manufacturer's region being joined to said absorbent article and said user's region extending beyond said longitudinal side edge of said absorbent article; said user's region having a proximal region to said longitudinal side edge and a distal region to said longitudinal side edge; said proximal region comprising an adhesive fastening member and said distal region comprising a mechanical fastening member; said adhesive fastening member and said mechanical fastening member having their respective fastening surfaces oriented in the direction of said inside surface of said body portion; said user's region being folded onto said inside surface of said body portion in said transport configuration;

a mechanical fastening landing member for cooperation with said mechanical fastening member of said adhesive-mechanical fastening tape tab, said landing member being disposed in said second end region and joined to said outside surface of said absorbent article;

a release tape being disposed on said inside surface for cooperation with said adhesive fastening member of said user's region in said transport configuration;

said release tape having a laterally innermost edge disposed laterally outwardly of said fastening surface of said mechanical fastening member in said transport configuration; and a delamination introducing area adapted to provide a non-adhesive surface, said delamination introducing area being disposed between the fastening surfaces of said adhesive fastening member and said mechanical fastening member in said users region whereby, in said transport configuration, said delamination introducing area is positioned so as to overlie the laterally innermost edge of said release tape.

2. A disposable absorbent article according to claim 1 wherein said delamination introducing area extends from about 3 mm to about 10 mm in a laterally outward direction from said laterally innermost edge of said release tape.

3. A disposable absorbent article according to claim 2 wherein said delamination introducing area extends from about 5 mm to about 7 mm in a laterally outward direction from said laterally innermost edge of said release tape.

4. A disposable absorbent article according to claim 2 wherein said release tape extends outwardly of said longitudinal side edge of said absorbent article and is joined to said adhesive fastening member to form a Y-bond.

5. A disposable absorbent article according to claim 2 wherein said release tape is joined to said inside surface of said absorbent article by an adhesive.

6. A disposable absorbent article according to claim 2 wherein said user's region and said manufacturer's region of said adhesive-mechanical fastening tape tab are continuous and have a continuous adhesive layer, said manufacturer's region being secured to said outside surface of said absorbent article by said continuous adhesive layer.

7. A disposable absorbent article according to claim 2 wherein said mechanical fastening member comprises hook-type engaging means and the mechanical fastening landing member comprises loop-type engaging means adapted to engage with said hook-type engaging means during use of said absorbent article.

8. A disposable absorbent article according to claim 1 wherein said mechanical fastening member comprises a base material and protruding mechanical elements such that said base material provides said non adhesive surface of said delamination introducing area.

9. A disposable absorbent article according to claim 8 wherein said delamination introducing area extends from 3 mm to 10 mm laterally outwardly from said laterally innermost edge of said release tape to overlie said release tape in a transport configuration.

10. A disposable absorbent article according to claim 9 wherein said delamination introducing area extends from about 5 mm to about 7 mm in a laterally outward direction from said laterally innermost edge of said release tape.

11. A disposable absorbent article according to claim 8 wherein said release tape extends laterally outwardly of said longitudinal side edge of said absorbent article and is joined to said adhesive fastening member to form a Y-bond.

12. A disposable absorbent article according to claim 8 wherein said release tape is joined to said inside surface of said absorbent article by an adhesive.

13. A disposable absorbent article according to claim 8 wherein said user's region and said manufacturer's region of said adhesive-mechanical fastening tape tab are continuous and have a continuous adhesive layer, said manufacturer's region being secured to said outside surface of said absorbent article by said continuous adhesive layer.

14. A disposable absorbent article according to claim 8 wherein said mechanical fastening member comprises hook-type engaging means and the mechanical fastening landing member comprises loop-type engaging means to engage with said hook-type engaging means during use of said absorbent article.

15. A disposable absorbent article according to claim 1 in the form of a disposable diaper wherein said body portion comprises a liquid pervious topsheet forming the inside surface;

a liquid impervious backsheet forming the outside surface and being joined to said topsheet; and an absorbent core disposed between said topsheet and said backsheet.

* * * * *